(12) United States Patent
Al-Ali et al.

(10) Patent No.: US 8,315,683 B2
(45) Date of Patent: Nov. 20, 2012

(54) DUO CONNECTOR PATIENT CABLE

(75) Inventors: Ammar Al-Ali, Tustin, CA (US); Yassir Abdul-Hafiz, Irvine, CA (US); Kevin Forrest, Rancho Santa Margarita, CA (US)

(73) Assignee: Masimo Corporation, Irvine, CA (US)

( * ) Notice: Subject to any disclaimer, the term of this patent is extended or adjusted under 35 U.S.C. 154(b) by 1461 days.

(21) Appl. No.: 11/858,818

(22) Filed: Sep. 20, 2007

(65) Prior Publication Data
US 2008/0071153 A1    Mar. 20, 2008

Related U.S. Application Data

(60) Provisional application No. 60/846,260, filed on Sep. 20, 2006.

(51) Int. Cl.
*A61B 5/1455*    (2006.01)
(52) U.S. Cl. .................. 600/323; 600/310; 600/322
(58) Field of Classification Search .................. 600/310, 600/323, 326, 322, 344; 439/188, 378, 489, 439/76, 502, 638; 356/41
See application file for complete search history.

(56) References Cited

U.S. PATENT DOCUMENTS

| | | | |
|---|---|---|---|
| 4,960,128 A | 10/1990 | Gordon et al. | |
| 4,964,408 A | 10/1990 | Hink et al. | |
| 5,041,187 A | 8/1991 | Hink et al. | |
| 5,069,213 A | 12/1991 | Polczynski | |
| 5,163,438 A | 11/1992 | Gordon et al. | |
| 5,297,548 A * | 3/1994 | Pologe | 600/310 |
| 5,337,744 A | 8/1994 | Branigan | |
| 5,341,805 A | 8/1994 | Stavridi et al. | |
| D353,195 S | 12/1994 | Savage et al. | |
| D353,196 S | 12/1994 | Savage et al. | |
| 5,377,676 A | 1/1995 | Vari et al. | |
| D359,546 S | 6/1995 | Savage et al. | |
| 5,431,170 A | 7/1995 | Mathews | |
| D361,840 S | 8/1995 | Savage et al. | |
| 5,443,390 A * | 8/1995 | Kokkosoulis et al. | 439/76.1 |
| D362,063 S | 9/1995 | Savage et al. | |
| 5,452,717 A | 9/1995 | Branigan et al. | |
| D363,120 S | 10/1995 | Savage et al. | |
| 5,456,252 A | 10/1995 | Vari et al. | |
| 5,482,036 A | 1/1996 | Diab et al. | |
| 5,490,505 A | 2/1996 | Diab et al. | |
| 5,494,043 A | 2/1996 | O'Sullivan et al. | |
| 5,533,511 A | 7/1996 | Kaspari et al. | |
| 5,561,275 A | 10/1996 | Savage et al. | |
| 5,562,002 A | 10/1996 | Lalin | |
| 5,590,649 A | 1/1997 | Caro et al. | |
| 5,602,924 A | 2/1997 | Durand et al. | |
| 5,632,272 A | 5/1997 | Diab et al. | |
| 5,638,816 A | 6/1997 | Kiani-Azarbayjany et al. | |
| 5,638,818 A | 6/1997 | Diab et al. | |
| 5,645,440 A | 7/1997 | Tobler et al. | |
| 5,685,299 A | 11/1997 | Diab et al. | |

(Continued)

*Primary Examiner* — Eric Winakur
*Assistant Examiner* — Chu Chuan (JJ) Liu
(74) *Attorney, Agent, or Firm* — Knobbe Martens Olson & Bear LLP

(57) ABSTRACT

A patient cable has a duo sensor connector having a first socket section and a second socket section. The first socket section is configured to removably attach a two-wavelength sensor. The second socket section in conjunction with the first socket section is configured to removably attach a multiple wavelength sensor in lieu of the two-wavelength sensor. A circuit housed in the duo sensor connector converts emitter array drive signals adapted for the multiple wavelength sensor into back-to-back emitter drive signals adapted for the two-wavelength sensor when attached.

11 Claims, 16 Drawing Sheets

U.S. PATENT DOCUMENTS

| | | | |
|---|---|---|---|
| D393,830 S | 4/1998 | Tobler et al. | |
| 5,743,262 A | 4/1998 | Lepper, Jr. et al. | |
| 5,758,644 A | 6/1998 | Diab et al. | |
| 5,760,910 A | 6/1998 | Lepper, Jr. et al. | |
| 5,769,785 A | 6/1998 | Diab et al. | |
| 5,782,757 A | 7/1998 | Diab et al. | |
| 5,785,659 A | 7/1998 | Caro et al. | |
| 5,791,347 A | 8/1998 | Flaherty et al. | |
| 5,810,734 A | 9/1998 | Caro et al. | |
| 5,823,950 A | 10/1998 | Diab et al. | |
| 5,830,131 A | 11/1998 | Caro et al. | |
| 5,833,618 A | 11/1998 | Caro et al. | |
| 5,860,919 A | 1/1999 | Kiani-Azarbayjany et al. | |
| 5,890,929 A | 4/1999 | Mills et al. | |
| 5,904,654 A | 5/1999 | Wohltmann et al. | |
| 5,919,134 A | 7/1999 | Diab | |
| 5,934,925 A | 8/1999 | Tobler et al. | |
| 5,940,182 A | 8/1999 | Lepper, Jr. et al. | |
| 5,995,855 A | 11/1999 | Kiani et al. | |
| 5,997,343 A | 12/1999 | Mills et al. | |
| 6,002,952 A | 12/1999 | Diab et al. | |
| 6,011,986 A | 1/2000 | Diab et al. | |
| 6,027,452 A | 2/2000 | Flaherty et al. | |
| 6,036,642 A | 3/2000 | Diab et al. | |
| 6,045,509 A | 4/2000 | Caro et al. | |
| 6,067,462 A | 5/2000 | Diab et al. | |
| 6,081,735 A | 6/2000 | Diab et al. | |
| 6,088,607 A | 7/2000 | Diab et al. | |
| 6,110,522 A | 8/2000 | Lepper, Jr. et al. | |
| 6,124,597 A | 9/2000 | Shehada | |
| 6,144,868 A | 11/2000 | Parker | |
| 6,151,516 A | 11/2000 | Kiani-Azarbayjany et al. | |
| 6,152,754 A | 11/2000 | Gerhardt et al. | |
| 6,157,850 A | 12/2000 | Diab et al. | |
| 6,165,005 A | 12/2000 | Mills et al. | |
| 6,184,521 B1 | 2/2001 | Coffin, IV et al. | |
| 6,206,830 B1 | 3/2001 | Diab et al. | |
| 6,229,856 B1 | 5/2001 | Diab et al. | |
| 6,232,609 B1 | 5/2001 | Snyder et al. | |
| 6,236,872 B1 | 5/2001 | Diab et al. | |
| 6,241,683 B1 | 6/2001 | Macklem et al. | |
| 6,256,523 B1 | 7/2001 | Diab et al. | |
| 6,263,222 B1 | 7/2001 | Diab et al. | |
| 6,278,522 B1 | 8/2001 | Lepper, Jr. et al. | |
| 6,280,213 B1 | 8/2001 | Tobler et al. | |
| 6,285,896 B1 | 9/2001 | Tobler et al. | |
| 6,321,100 B1 | 11/2001 | Parker | |
| 6,334,065 B1 | 12/2001 | Al-Ali et al. | |
| 6,343,224 B1 | 1/2002 | Parker | |
| 6,349,228 B1 | 2/2002 | Kiani et al. | |
| 6,360,114 B1 | 3/2002 | Diab et al. | |
| 6,368,283 B1 | 4/2002 | Xu et al. | |
| 6,371,921 B1 | 4/2002 | Caro et al. | |
| 6,377,829 B1 | 4/2002 | Al-Ali | |
| 6,388,240 B2 | 5/2002 | Schulz et al. | |
| 6,397,091 B2 | 5/2002 | Diab et al. | |
| 6,430,525 B1 | 8/2002 | Weber et al. | |
| 6,463,311 B1 | 10/2002 | Diab | |
| 6,470,199 B1 | 10/2002 | Kopotic et al. | |
| 6,501,975 B2 | 12/2002 | Diab et al. | |
| 6,505,059 B1 | 1/2003 | Kollias et al. | |
| 6,515,273 B2 | 2/2003 | Al-Ali | |
| 6,519,487 B1 | 2/2003 | Parker | |
| 6,525,386 B1 | 2/2003 | Mills et al. | |
| 6,526,300 B1 | 2/2003 | Kiani et al. | |
| 6,541,756 B2 | 4/2003 | Schulz et al. | |
| 6,542,764 B1 | 4/2003 | Al-Ali et al. | |
| 6,580,086 B1 | 6/2003 | Schulz et al. | |
| 6,584,336 B1 | 6/2003 | Ali et al. | |
| 6,595,316 B2 | 7/2003 | Cybulski et al. | |
| 6,597,932 B2 | 7/2003 | Tian et al. | |
| 6,597,933 B2 | 7/2003 | Kiani et al. | |
| 6,606,511 B1 | 8/2003 | Ali et al. | |
| 6,632,181 B2 | 10/2003 | Flaherty et al. | |
| 6,639,668 B1 | 10/2003 | Trepagnier | |
| 6,640,116 B2 | 10/2003 | Diab | |
| 6,643,530 B2 | 11/2003 | Diab et al. | |
| 6,650,917 B2 | 11/2003 | Diab et al. | |
| 6,654,624 B2 | 11/2003 | Diab et al. | |
| 6,658,276 B2 | 12/2003 | Kianl et al. | |
| 6,661,161 B1 | 12/2003 | Lanzo et al. | |
| 6,671,531 B2 | 12/2003 | Al-Ali et al. | |
| 6,678,543 B2 | 1/2004 | Diab et al. | |
| 6,684,090 B2 | 1/2004 | Ali et al. | |
| 6,684,091 B2 | 1/2004 | Parker | |
| 6,697,656 B1 | 2/2004 | Al-Ali | |
| 6,697,657 B1 | 2/2004 | Shehada et al. | |
| 6,697,658 B2 | 2/2004 | Al-Ali | |
| RE38,476 E | 3/2004 | Diab et al. | |
| 6,699,194 B1 | 3/2004 | Diab et al. | |
| 6,714,804 B2 | 3/2004 | Al-Ali et al. | |
| RE38,492 E | 4/2004 | Diab et al. | |
| 6,721,582 B2 | 4/2004 | Trepagnier et al. | |
| 6,721,585 B1 | 4/2004 | Parker | |
| 6,725,075 B2 | 4/2004 | Al-Ali | |
| 6,728,560 B2 | 4/2004 | Kollias et al. | |
| 6,735,459 B2 | 5/2004 | Parker | |
| 6,745,060 B2 | 6/2004 | Diab et al. | |
| 6,760,607 B2 | 7/2004 | Al-Ali | |
| 6,770,028 B1 | 8/2004 | Ali et al. | |
| 6,771,994 B2 | 8/2004 | Kiani et al. | |
| 6,792,300 B1 | 9/2004 | Diab et al. | |
| 6,813,511 B2 | 11/2004 | Diab et al. | |
| 6,816,741 B2 | 11/2004 | Diab | |
| 6,822,564 B2 | 11/2004 | Al-Ali | |
| 6,826,419 B2 | 11/2004 | Diab et al. | |
| 6,830,711 B2 | 12/2004 | Mills et al. | |
| 6,850,787 B2 | 2/2005 | Weber et al. | |
| 6,850,788 B2 | 2/2005 | Al-Ali | |
| 6,852,083 B2 | 2/2005 | Caro et al. | |
| 6,861,639 B2 | 3/2005 | Al-Ali | |
| 6,898,452 B2 | 5/2005 | Al-Ali et al. | |
| 6,920,345 B2 | 7/2005 | Al-Ali et al. | |
| 6,931,268 B1 | 8/2005 | Kiani-Azarbayjany et al. | |
| 6,934,570 B2 | 8/2005 | Kiani et al. | |
| 6,939,305 B2 | 9/2005 | Flaherty et al. | |
| 6,943,348 B1 | 9/2005 | Coffin IV | |
| 6,950,687 B2 | 9/2005 | Al-Ali | |
| 6,961,598 B2 | 11/2005 | Diab | |
| 6,970,792 B1 | 11/2005 | Diab | |
| 6,979,812 B2 | 12/2005 | Al-Ali | |
| 6,985,764 B2 | 1/2006 | Mason et al. | |
| 6,993,371 B2 | 1/2006 | Kiani et al. | |
| 6,996,427 B2 | 2/2006 | Ali et al. | |
| 6,999,904 B2 | 2/2006 | Weber et al. | |
| 7,003,338 B2 | 2/2006 | Weber et al. | |
| 7,003,339 B2 | 2/2006 | Diab et al. | |
| 7,015,451 B2 | 3/2006 | Dalke et al. | |
| 7,024,233 B2 | 4/2006 | Ali et al. | |
| 7,027,849 B2 | 4/2006 | Al-Ali | |
| 7,030,749 B2 | 4/2006 | Al-Ali | |
| 7,039,449 B2 | 5/2006 | Al-Ali | |
| 7,041,060 B2 | 5/2006 | Flaherty et al. | |
| 7,044,918 B2 | 5/2006 | Diab | |
| 7,067,893 B2 | 6/2006 | Mills et al. | |
| 7,096,052 B2 | 8/2006 | Mason et al. | |
| 7,096,054 B2 | 8/2006 | Abdul-Hafiz et al. | |
| 7,132,641 B2 | 11/2006 | Schulz et al. | |
| 7,142,901 B2 | 11/2006 | Kiani et al. | |
| 7,149,561 B2 | 12/2006 | Diab | |
| 7,186,966 B2 | 3/2007 | Al-Ali | |
| 7,190,261 B2 | 3/2007 | Al-Ali | |
| 7,215,984 B2 | 5/2007 | Diab | |
| 7,215,986 B2 | 5/2007 | Diab | |
| 7,221,971 B2 | 5/2007 | Diab | |
| 7,225,006 B2 | 5/2007 | Al-Ali | |
| 7,225,007 B2 | 5/2007 | Al-Ali | |
| RE39,672 E | 6/2007 | Shehada et al. | |
| 7,239,905 B2 | 7/2007 | Kiani-Azarbayjany et al. | |
| 7,245,953 B1 | 7/2007 | Parker | |
| 7,254,431 B2 | 8/2007 | Al-Ali | |
| 7,254,433 B2 | 8/2007 | Diab et al. | |
| 7,254,434 B2 | 8/2007 | Schulz et al. | |
| 7,272,425 B2 | 9/2007 | Al-Ali | |
| 2007/0149864 A1* | 6/2007 | Laakkonen | 600/323 |

* cited by examiner

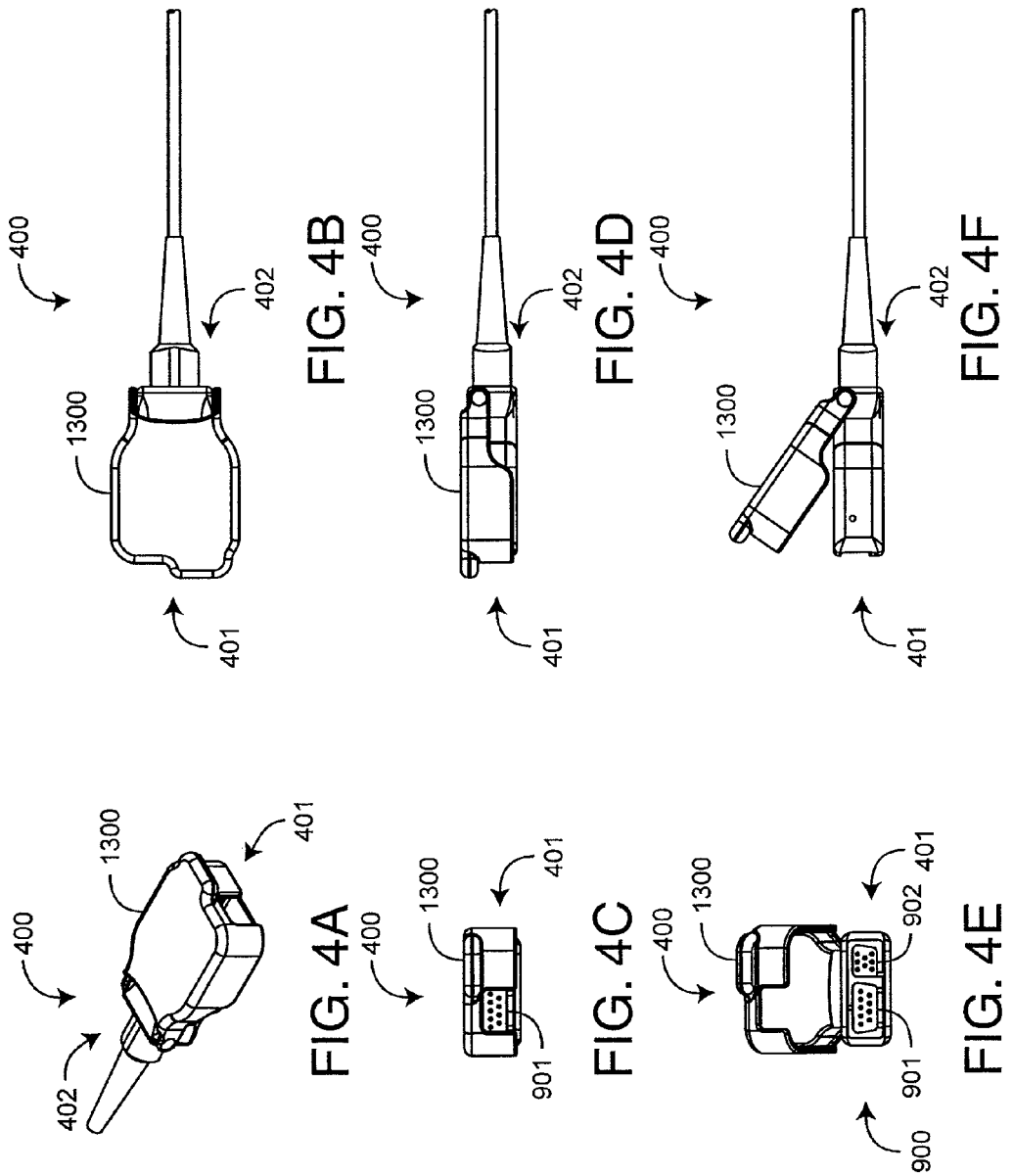

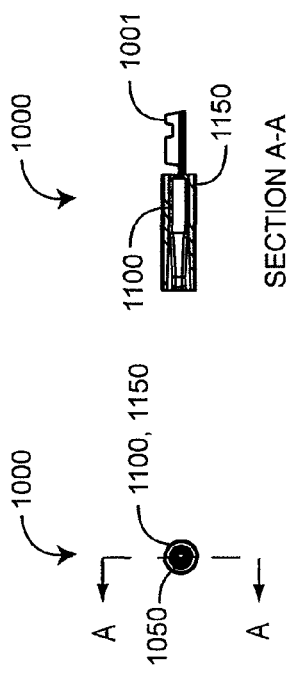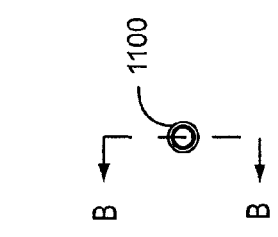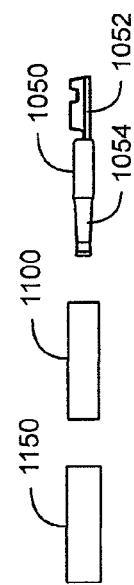

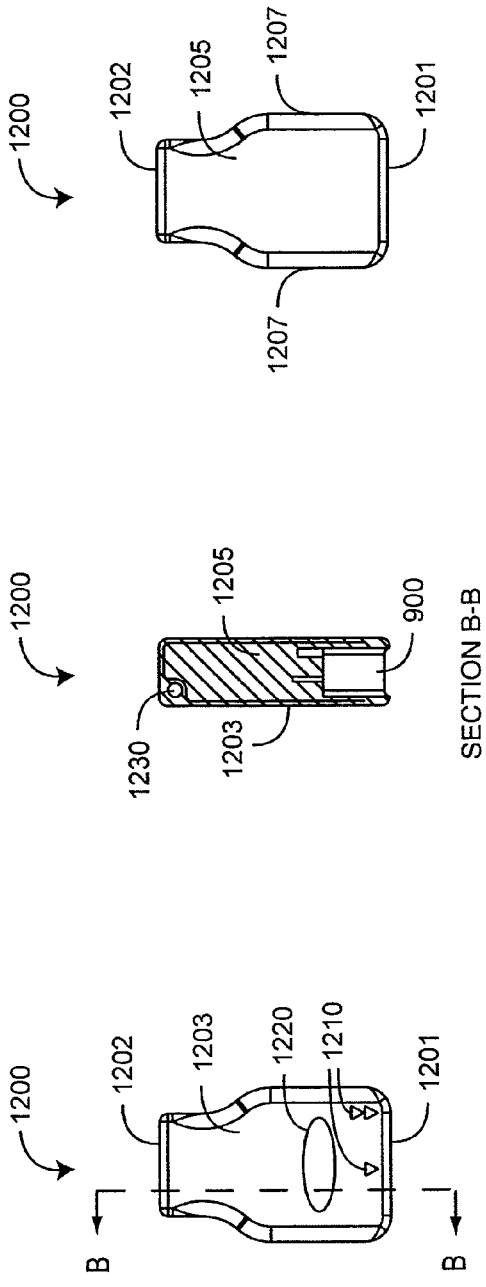
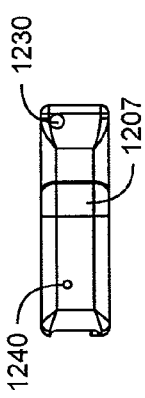
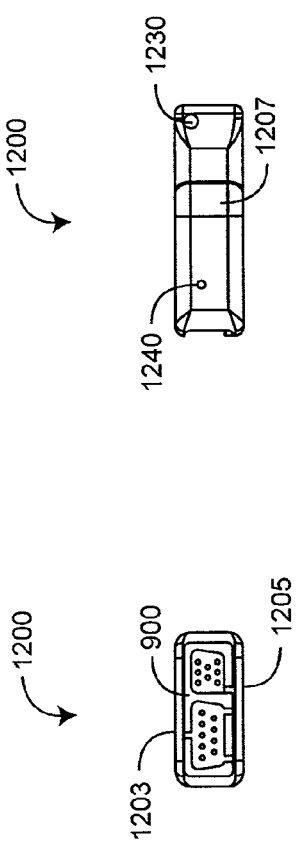
FIG. 12C
FIG. 12B
FIG. 12E
FIG. 12A
FIG. 12D

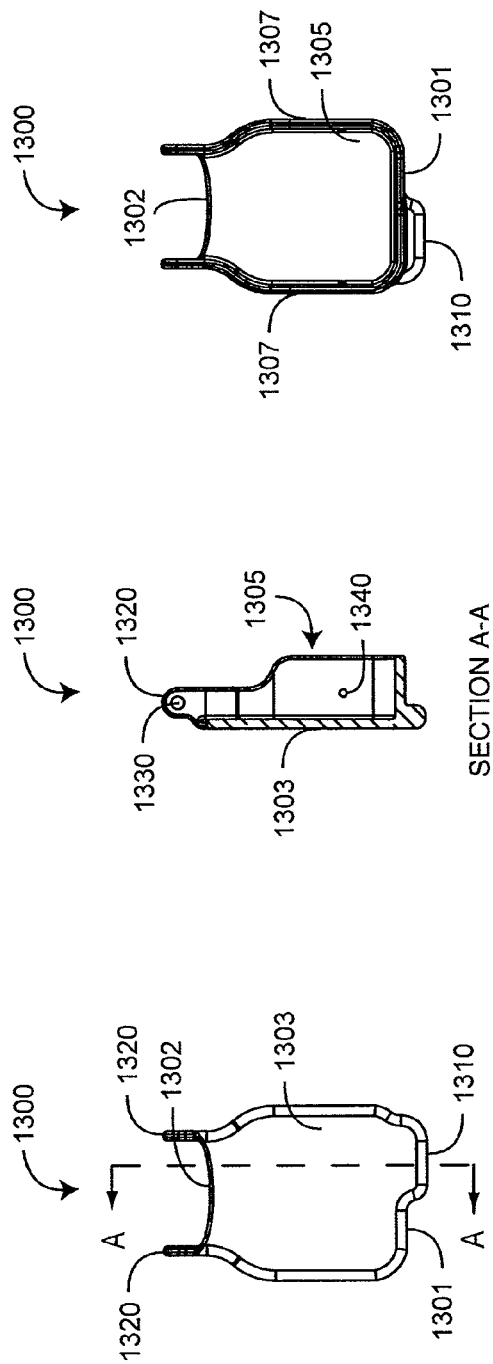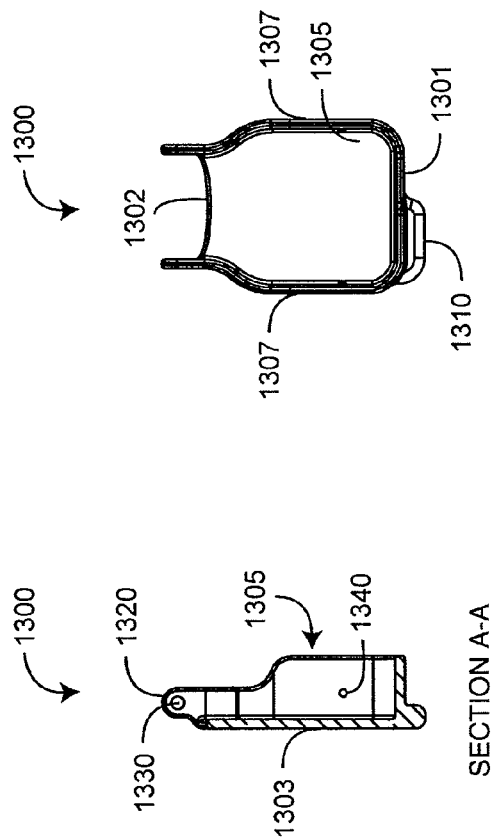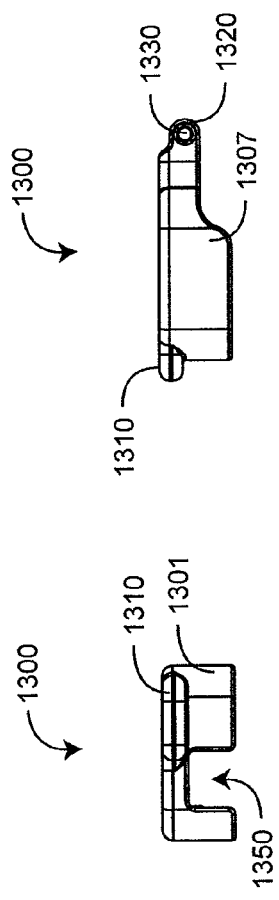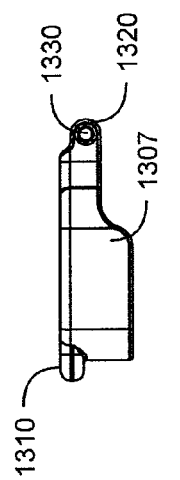

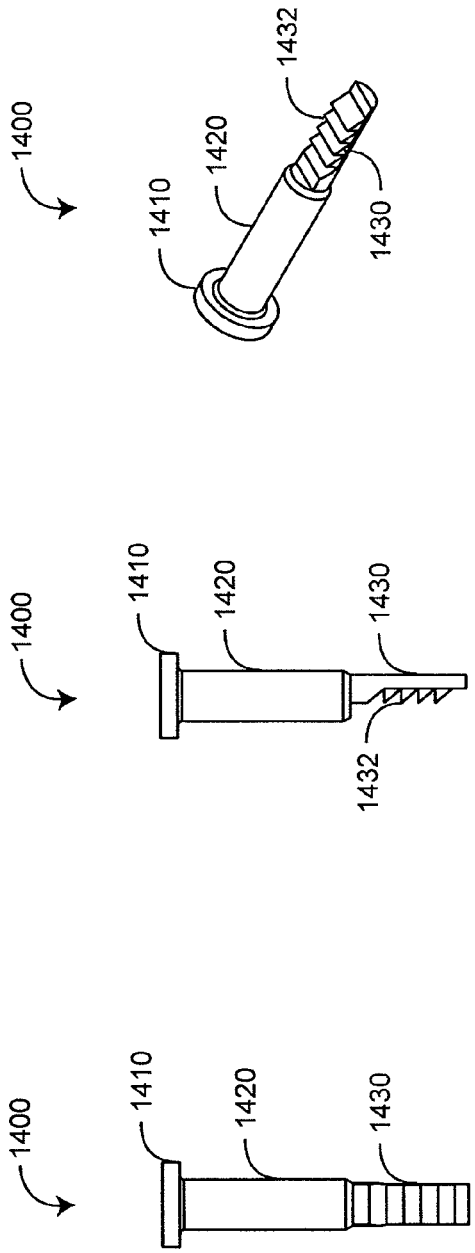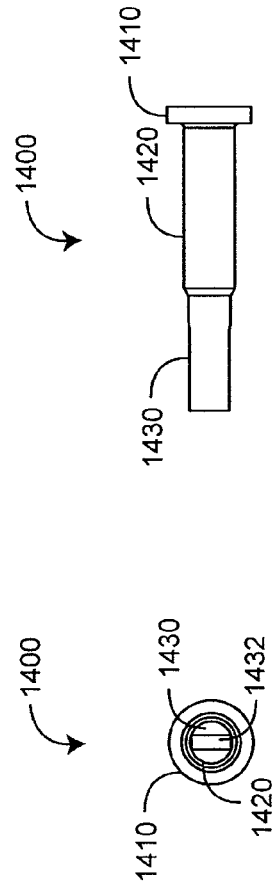

DUO CONNECTOR PATIENT CABLE

REFERENCE TO RELATED APPLICATION

The present application claims priority benefit under 35 U.S.C. §119(e) from U.S. Provisional Application No. 60/846,260, filed Sep. 20, 2006, entitled "Duo Connector Patient Cable," which is incorporated herein by reference.

BACKGROUND OF THE INVENTION

Pulse oximetry provides a noninvasive procedure for measuring the oxygen status of circulating blood and has gained rapid acceptance in a wide variety of medical applications, including surgical wards, intensive care and neonatal units, general wards, and home care and physical training. A pulse oximetry system has a physiological sensor applied to a patient, a monitor, and a patient cable connecting the sensor and the monitor. The sensor has light emitters and a detector, which are attached to a tissue site, such as a finger. The patient cable transmits emitter drive signals from the monitor to the sensor. The emitters respond to the drive signals so as to transmit light into the tissue site. The detector is responsive to the emitted light after attenuation by pulsatile blood flowing in the tissue site, generating a detector signal to the monitor. The monitor processes the detector signal to provide a numerical readout of physiological parameters such as oxygen saturation ($SpO_2$) and pulse rate.

FIG. 1 illustrates portions of a pulse oximetry system 100 having a monitor 110, a sensor 120 and a patient cable 130 interconnecting the monitor 110 and sensor 120. The sensor 120 has LEDs 121, 125 capable of emitting light having two wavelengths into a tissue site. The LEDs 121,125 are configured in a back-to-back arrangement so that a first contact 132 is connected to a first LED cathode 122 and a second LED anode 127. A second contact 134 is connected to a first LED anode 123 and a second LED cathode 126. The monitor 110 has a first driver 112 and a second driver 114. The first contact 132 is in communications with a first driver 112 and the second contact 134 is in communications with a second driver 114. The first LED 121 is activated when the first driver 112 is pulled to Vcc and the second driver 114 provides a current sink to ground. The second LED 125 is activated when the second driver 114 is pulled to Vcc and the first driver 112 provides a current sink to ground. Pulse oximeters capable of reading through motion induced noise are available from Masimo Corporation ("Masimo") of Irvine, Calif. Pulse oximeters capable of reading through motion induced noise are also disclosed in at least U.S. Pat. Nos. 6,770,028, 6,658, 276, 6,157,850, 6,002,952 5,769,785, and 5,758,644, which are assigned to Masimo and are incorporated by reference herein.

SUMMARY OF THE INVENTION

A physiological measurement system can also be a multiple parameter monitor and a multiple wavelength sensor that provide enhanced measurement capabilities as compared with conventional pulse oximetry. The physiological measurement system allows the measurement of blood constituents and related parameters in addition to oxygen saturation and pulse rate, such as carboxyhemoglobin (HbCO) and methemoglobin (HbMet) to name a few.

FIG. 2 illustrates a multiple parameter system 200 having a multiple parameter monitor 210, a multiple wavelength sensor 220 and a patient cable 230 interconnecting the monitor 210 and sensor 220. The sensor 220 has an emitter array 262 having multiple LEDs 264 together capable of emitting light having multiple wavelengths into a tissue site. Anode drivers 232 and cathode drivers 234 are electrically connected to the LEDs 264 and activate LEDs by addressing at least one row 266 and at least one column 268 of an electrical grid. In an embodiment, the emitter array 262 has LEDs 264 connected within an electrical grid of n rows and m columns totaling n+m drive lines, where n and m integers greater than one. In an embodiment, the emitter array 262 comprises up to sixteen LEDs 264 configured in an electrical grid of four rows and four columns. Each of the four anode drive lines 272 provide a common anode connection to four LEDs 264, and each of the four cathode drive lines 274 provide a common cathode connection to four LEDs 264. Thus, the sixteen LEDs 264 are advantageously driven with only eight wires, including four anode drive lines 272 and four cathode 274 drive lines.

Also shown in FIG. 2, anode drivers 212 and cathode drivers 214 located in the monitor 210 selectively activate the LEDs 264. In particular, anode and cathode drivers function together as switches to Vcc and current sinks, respectively, to activate LEDs 264 and as switches to ground and Vcc, respectively, to deactivate LEDs. This push-pull drive configuration prevents parasitic current flow in deactivated LEDs. In a particular embodiment, only one anode drive line 232 is switched to Vcc at a time. One to four cathode drive lines 234, however, can be simultaneously switched to a current sink so as to simultaneously activate multiple LEDs within a particular row. Multiple parameter monitors and multiple wavelength sensors capable of measuring blood constituents such as carboxyhemoglobin (HbCO) and methemoglobin (HbMet) are available from Masimo. Further, multiple parameter monitors and multiple wavelength sensors are disclosed in at least U.S. patent application Ser. Nos. 11/367,033 and 11/367,013, which are assigned to Masimo Laboratories, Irvine, Calif. and are incorporated by reference herein.

A duo connector patient cable is advantageously configured to accommodate either of two types of mating sensor connectors including a conventional connector for a pulse oximetry sensor and a multiple wavelength sensor connector. Further, a duo connector patient cable advantageously converts drive signals for array configured emitters into drive signals for back-to-back configured emitters. In additional, a duo connector patient cable advantageously reconfigures connector pinouts for a multiple wavelength sensor to optimize signal-to-noise ratio (SNR) performance.

BRIEF DESCRIPTION OF THE DRAWINGS

FIGS. 4A-F are perspective, top, front, side, retainer hinged-open front and retainer hinged-open side views of a duo connector, respectively;

FIGS. 10A-D are top, front, side cross sectional and side exploded views, respectively, of a detector socket pin;

FIGS. 11A-C are top, front and side cross sections views, respectively, of a detector socket pin shroud;

FIGS. 11D-E are front and side views, respectively, of a detector socket pin shield;

FIGS. 12A-E are top, side cross sectional, bottom, front and side views, respectively, of a duo connector shell overmolded on a socket;

FIGS. 13A-E are top, side cross sectional, bottom, front and bottom views, respectively, of a duo connector retainer;

FIGS. 14A-E are top, side, perspective, front and side views, respectively, of a duo connector hinge pin.

DETAILED DESCRIPTION OF THE PREFERRED EMBODIMENTS

Figure 3A:
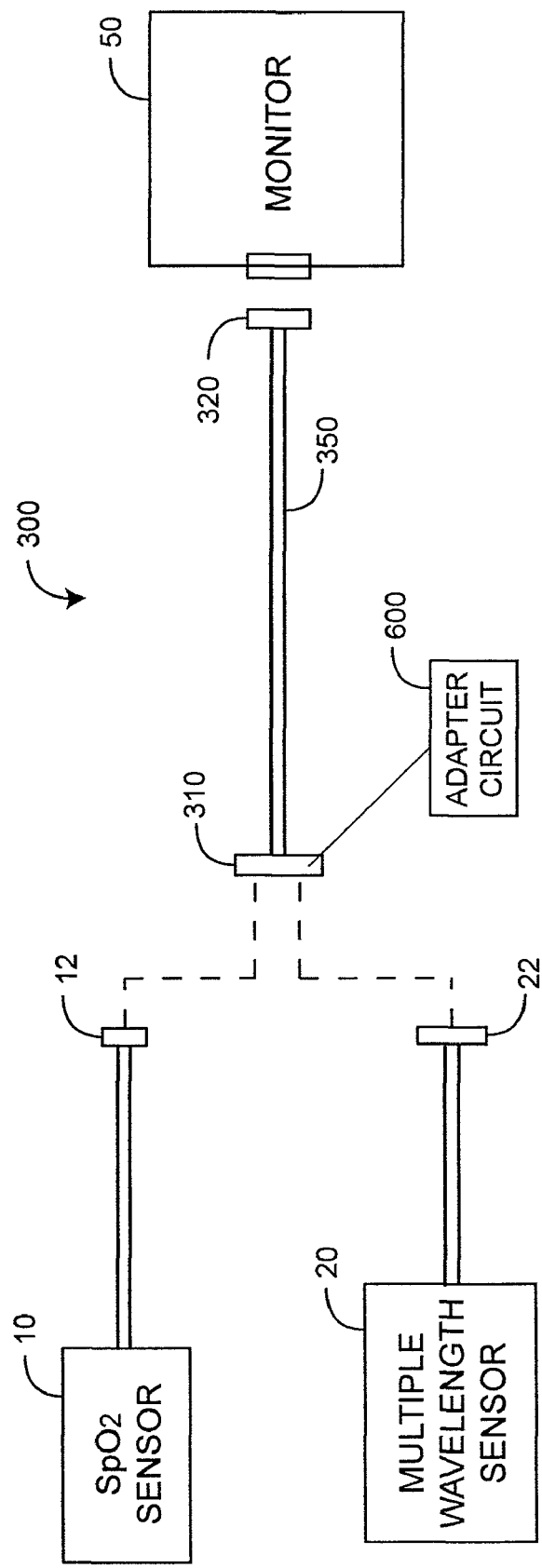
FIG. 3A is a general block diagram of a duo connector patient cable utilized by a patient monitoring system.

FIG. 3A generally illustrates a duo connector patient cable 300 as part of a patient monitoring system. Advantageously, the duo connector patient cable 300 allows both a $SpO_2$ sensor 10 and a multiple wavelength sensor 20 to communicate with a multiple parameter monitor 50. In particular, a duo connector 310 accepts both a conventional pulse oximetry sensor and a multiple wavelength sensor, each having different connectors 12, 22. In an embodiment, the duo connector accepts a WTM LNCS® low noise enabled sensor and a RAINBOW™ multiple wavelength sensor. LNCS® brand sensors and RAINBOW™ brand monitors and sensors are available from Masimo Corporation. In addition, the duo connector patient cable 300 has an adapter circuit 600 that converts array drive signals configured for a multiple wavelength sensor 20 so as to drive back-to-back emitters of a $SpO_2$ sensor 10. Further, the adapter circuit 600 reconfigures the duo connector patient cable 300 to a signal and ground pinout that has improved signal-to-noise ratio (SNR) and crosstalk performance when connected to a multiple wavelength sensor. An adapter circuit 600 is described in further detail with respect to FIGS. 6-7, below.

Figure 3B:
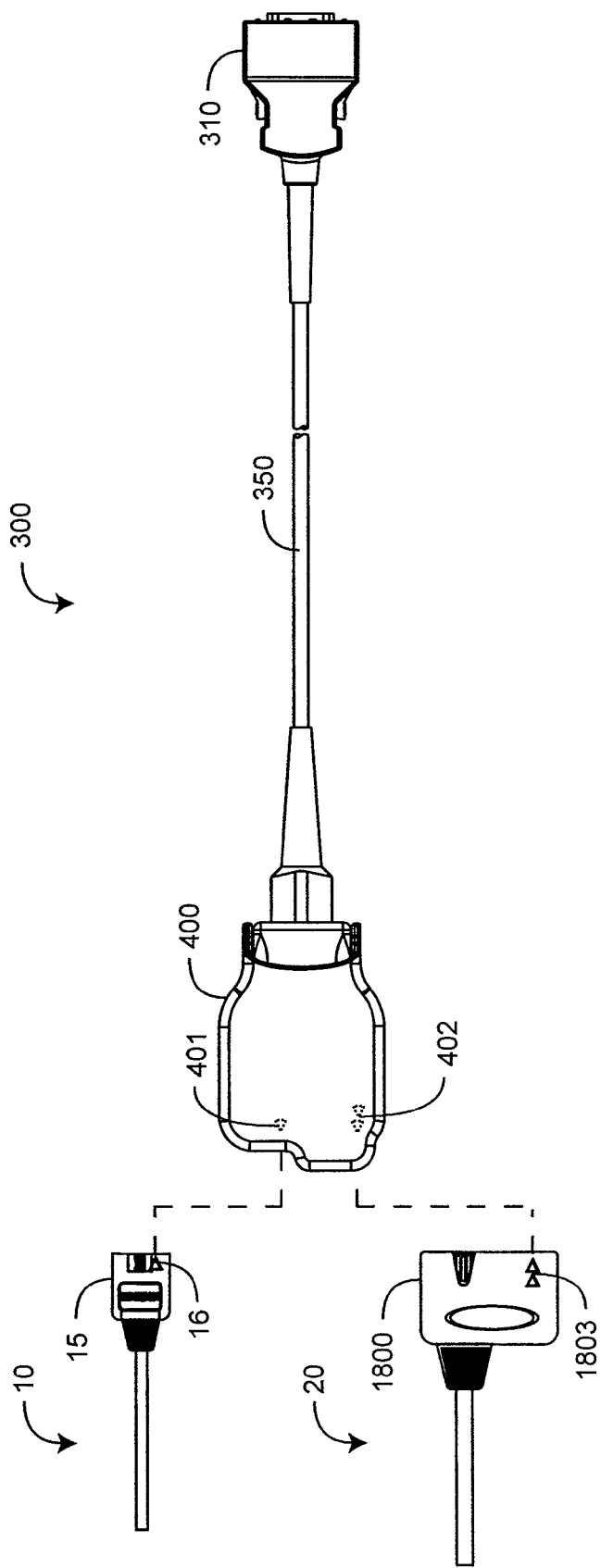
FIG. 3B is a top view of a duo connector patient cable embodiment that accommodates a conventional pulse oximetry sensor connector and a multiple wavelength sensor connector.

FIG. 3B illustrates a duo connector patient cable 300 having a duo connector 400, a monitor connector 310 and a cable 350 having wires that interconnect the duo connector 400 and monitor connector 310. The duo connector 400 advantageously accommodates a conventional $SpO_2$ sensor connector 15 and a multiple wavelength sensor connector 1800. In an embodiment, a $SpO_2$ sensor 10 is plugged into the patient cable 300 so that a $SpO_2$ sensor alignment arrow 16 matches a first patient cable alignment arrow 401. Also a multiple wavelength sensor 20 is plugged into the patient cable 300 so that a multiple wavelength sensor alignment arrow 1803 matches a second patient cable alignment arrow 402. The cable alignment arrows 401, 402 (shown hidden) are inscribed on a connector shell 1200 (FIG. 12A) covered by a retainer 1300 (FIGS. 13A-E) that is opened during sensor attachment. In an embodiment, the $SpO_2$ sensor connector 15 is a 9-pin mini-D connector, which is well-known in the art. The monitor connector 310 is a 20-pin DB connector, which is also well-known in the art and further described with respect to FIG. 5B, below. Physical aspects of the duo connector 400 are described generally with respect to FIGS. 4A-F and in greater detail with respect to FIGS. 8-15. The duo connector signals, grounds and pinouts are described with respect to FIGS. 5-7. The adapter circuit 600 (FIG. 6) for configuring the duo connector 400 to accommodate either a two-wavelength $SpO_2$ sensor or a multiple wavelength sensor is described with respect to FIGS. 6-7.

FIGS. 4A-F illustrate a duo connector 400 having a front 401 and a back 402. The front 401 has a socket 900 that accommodates either of two mating sensor plugs 15, 1800 (FIG. 3B). The back 402 terminates a cable 350 (FIG. 3B). The duo connector socket 900 has a first socket section 901 configured for a conventional $SpO_2$ sensor plug 15 (FIG. 3B) and a second socket section 902, which along with the first socket section 901 is configured for a multiple wavelength sensor plug 1800 (FIG. 3B). In particular, the first socket section 901 has pinouts for back-to-back LED drive signals from a monitor to a sensor and detector signals and sensor information from the sensor to the monitor. The second socket section 902 has pinouts for LED array drive signals from a monitor to a sensor. The pinouts for the socket sections 901, 902 are described in further detail with respect to FIGS. 5A-C, below. The duo connector 400 also has a retainer 1300 movable between a closed position (FIGS. 4A-D) and an open position (FIGS. 4E-F). In the open position, the retainer 1300 allows either sensor plug 15, 1800 (FIG. 3B) to be inserted into or removed from the socket 900. In the closed position, the retainer 1300 prevents either sensor plug 15, 1800 (FIG. 3B) from inadvertently disconnecting from the socket 900.

Figure 5A:
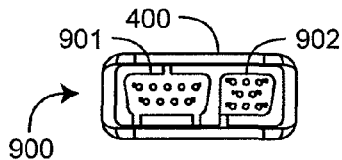
FIGS. 5A-C are a front view of a duo connector, a front view of a monitor connector and a schematic of a duo connector patient cable, respectively.
Figure 5B:
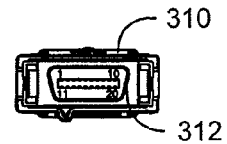
Figure 5C:
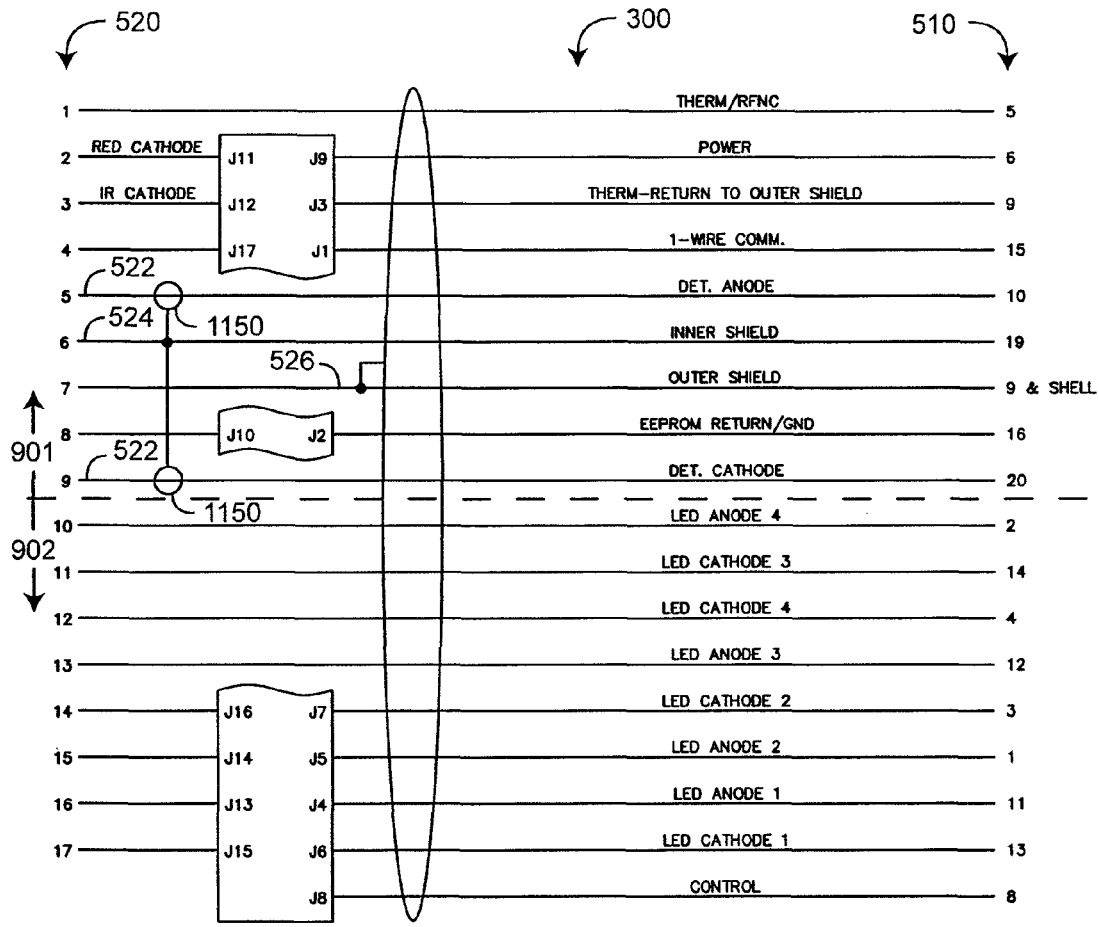

FIGS. 5A-C illustrate a duo connector patient cable 300. In particular, the socket 900 (FIG. 5A) and the corresponding sensor pinouts 520 (FIG. 5C) relate to the duo connector 400 (FIG. 5A). Also, the monitor socket 312 (FIG. 5B) and the corresponding monitor pinouts 510 relate to the monitor connector 310 (FIG. 5B). Also illustrated in is a circuit board 700 (FIG. 5C) that resides in the duo connector 400, as described with respect to FIGS. 7-8, below, and that switches the pinouts under monitor control according to the sensor 10, 20 (FIGS. 3A-B) plugged into the duo connector 400.

As shown in FIGS. 5A-C, the duo connector pinouts 520 are divided into pins 1-9, associated with a first socket section 901 and pins 10-17 associated with a second socket section 902. When a $SpO_2$ sensor 10 (FIGS. 3A-B) is inserted into the first socket section 901, the monitor detects the $SpO_2$ sensor from the "1-wire comm" line connecting the sensor side (pin 4) 520 and the monitor side (pin 15) 510. The monitor then sets the "control" line on pin 8 510 so that the circuit board 700 converts the first two LED cathode drive signals (pins 3, 13) 510 and LED anode drive signals (pins 1, 11) 510 to a red cathode drive signal (pin 2) 520 and an IR cathode drive signals (pin 3) 520.

Also as shown in FIGS. 5A-C, when a multiple wavelength sensor 20 (FIGS. 3A-B) is inserted into the socket sections 901, 902, the monitor detects the sensor from the "1-wire comm" line connecting the sensor side (pin 4) 520 and the monitor side (pin 15) 510. The monitor then sets the "control" line (pin 8) 510 so that the circuit board 700 grounds the now unused drive signal lines (pins 2, 3) 520. That is, for the higher performance multiple wavelength sensor 20 (FIGS. 3A-B), the detector signals (pins 5, 9) 520 on the first socket section 901 are advantageously isolated from the drive signals (pins 10-17) 520 on the second socket section 902. This reduces the possibility of cross-talk from drive lines to detector lines. Further, the detector signals (pins 5, 9) 522 are separately shielded 1150, and the shields 1150 are grounded to a cable inner shield (pin 6) 524, providing further noise immunity for the detector signal.

Figure 1:
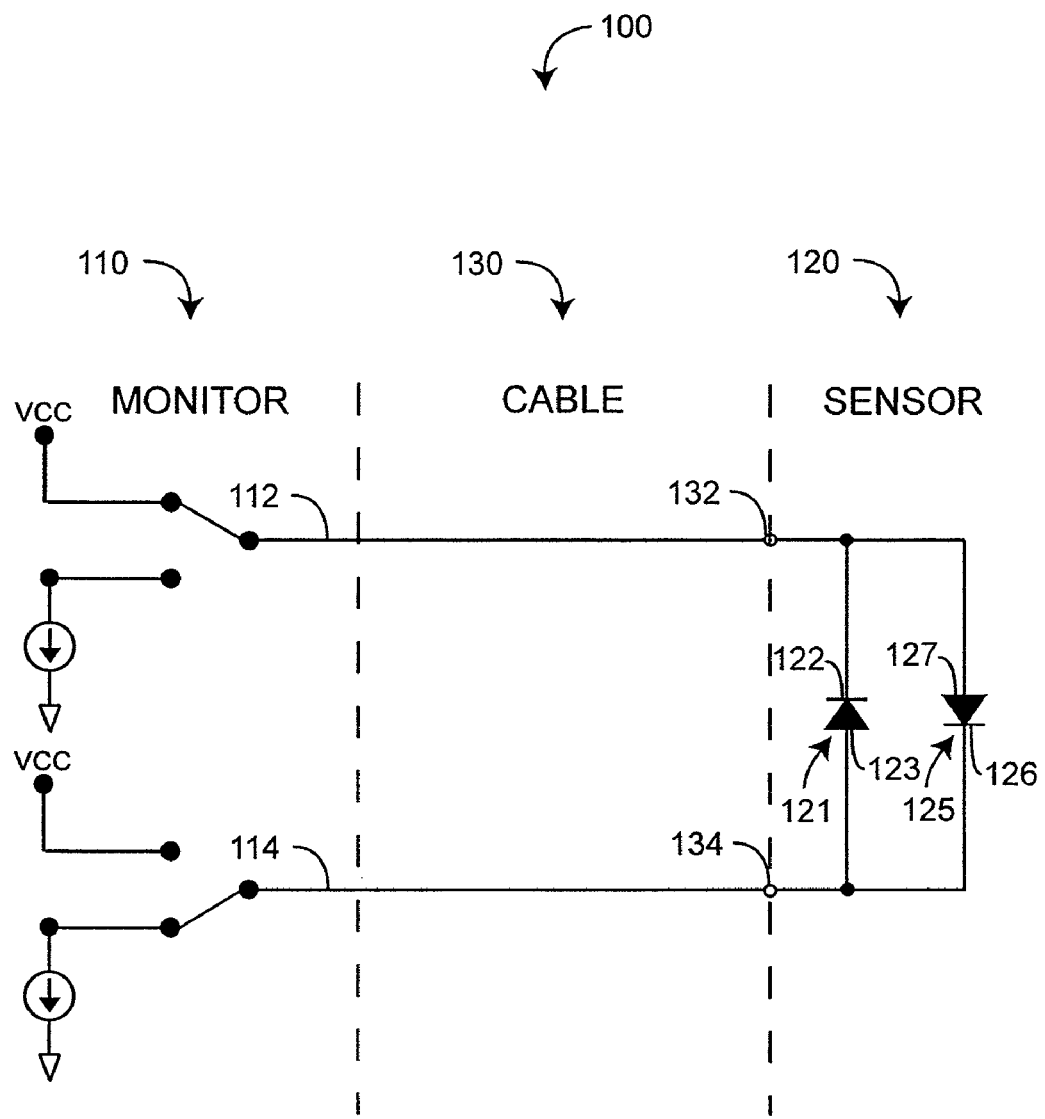
FIG. 1 is a block diagram of a conventional pulse oximetry system.
Figure 2:
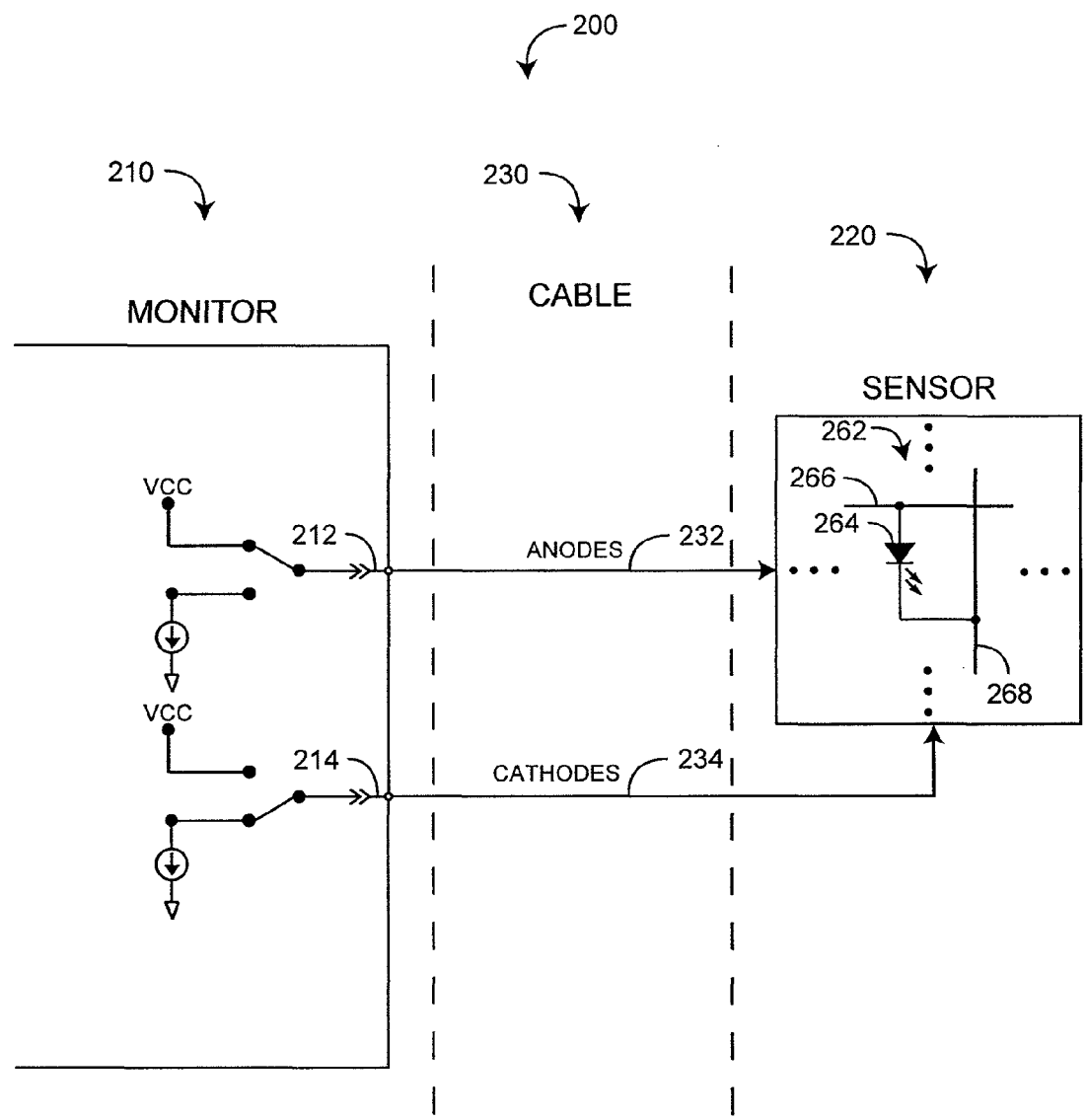
FIG. 2 is a block diagram of a multiple parameter system.
Figure 6:
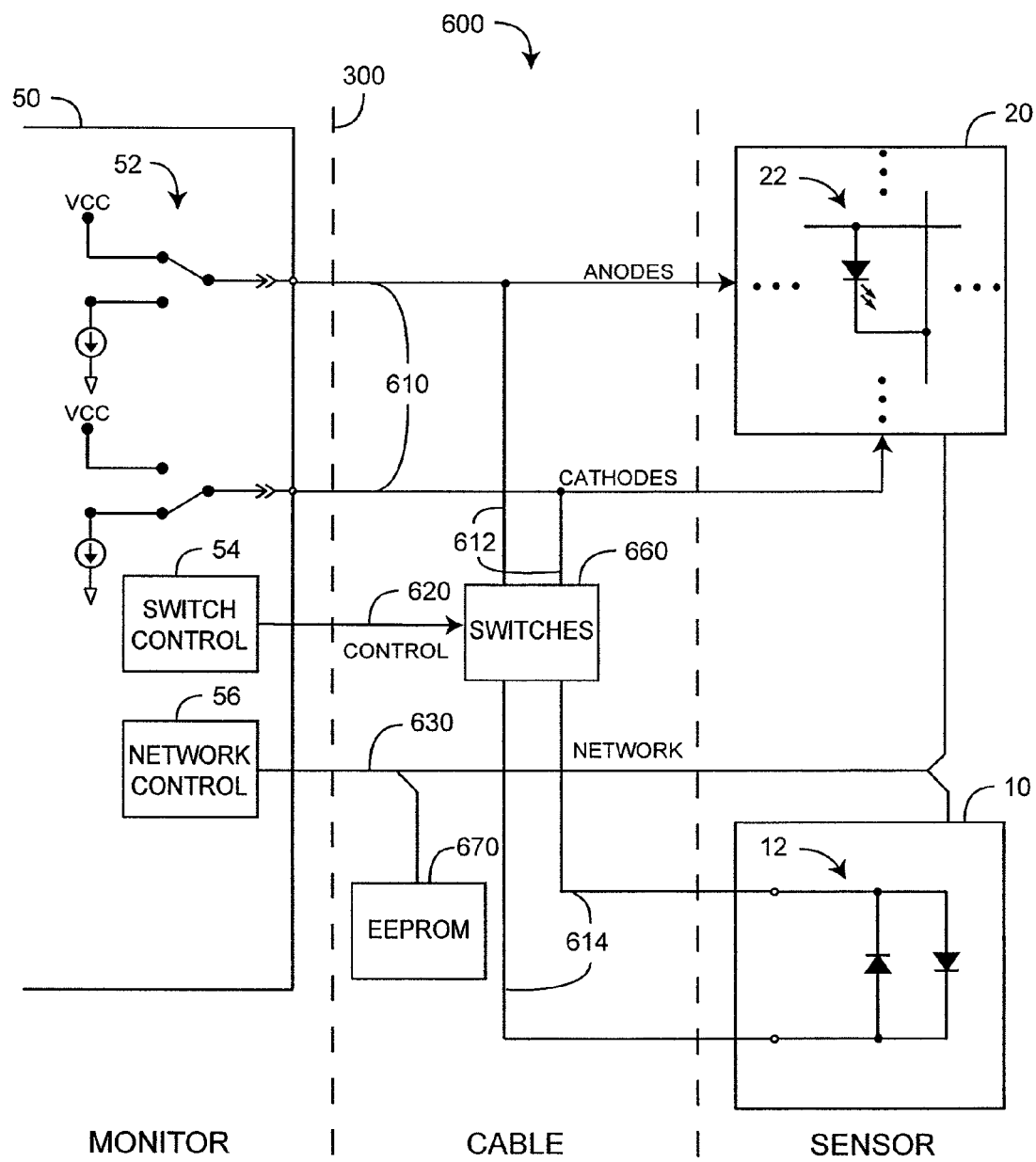
FIG. 6 is a block diagram of a multiple parameter patient monitoring system utilizing a duo connector patient cable.

FIG. 6 illustrates portions of a multiple parameter system embodiment having a multiple parameter monitor 50 and a duo connector patient cable 300 interconnecting either a $SpO_2$ sensor 10 or a multiple wavelength sensor 20. The duo connector patient cable 300 advantageously incorporates an adapter circuit 600 allowing the multiple parameter monitor 50 to drive either back-to-back (red and IR wavelength) LEDs 12 of a $SpO_2$ sensor 10 or a LED array 22 of a multiple wavelength sensor 20. In particular, the patient cable 300 has array lines 610 configured to communicate array drive signals 52 to a LED array 22, as described with respect to FIG. 2, above. The patient cable 300 also has an adapter circuit 600 that configures an array line subset 612 so as to communicate array drive signals 52 to back-to-back LEDs 12.

As shown in FIG. 6, the adapter circuit 600 incorporates switches 660 that selectively route the array line subset 612 so that the array drive signals 52 activate the back-to-back LEDs 12 when the monitor 50 senses a $SpO_2$ sensor 10 is connected to the patient cable 300. When the monitor 50 senses a multiple wavelength sensor 20 is connected to the patient cable 300, the switches 660 advantageously ground certain of the sensor connector pins (not shown) so as to minimize crosstalk between drive signals 52 and detector signals (not shown), as described in further detail below. In an embodiment, the monitor 50 utilizes eight array lines 610 to drive a four-by-four emitter array 22 of up to sixteen LEDs. Four of the array lines 612 are routed through the switches 660 to back-to-back lines 614, as described in further detail with respect to FIGS. 7A-B, below.

Also shown in FIG. 6, in an embodiment, a network controller 56 monitors a network 630 so as to read an information element from either sensor 10, 20 to identify either a $SpO_2$ sensor 10 or a multiple wavelength sensor 20. The network controller 56 can also read the EEPROM 670 over the network 630 so that the monitor 50 can identify a duo sensor patient cable 300 is attached. The monitor 50 also has a switch control 54 that provides a control 620 in response to information from the network 630. That is, the control 620 configures the switches 660 according to the sensor 10, 20 that is attached to the duo connector patient cable 300.

Figure 7A:
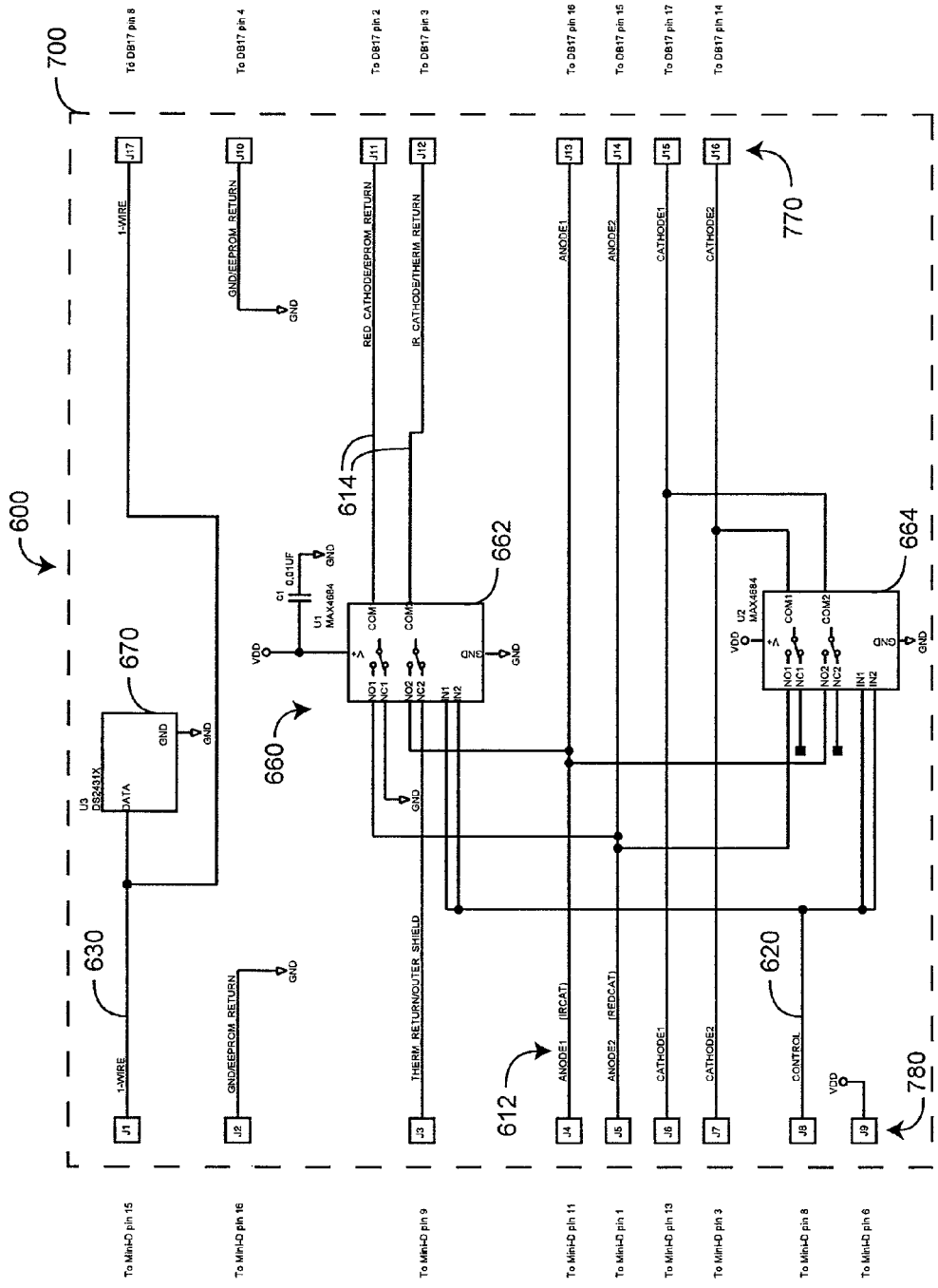
FIG. 7A is a block diagram of a duo connector patient cable circuit.
Figure 7B:
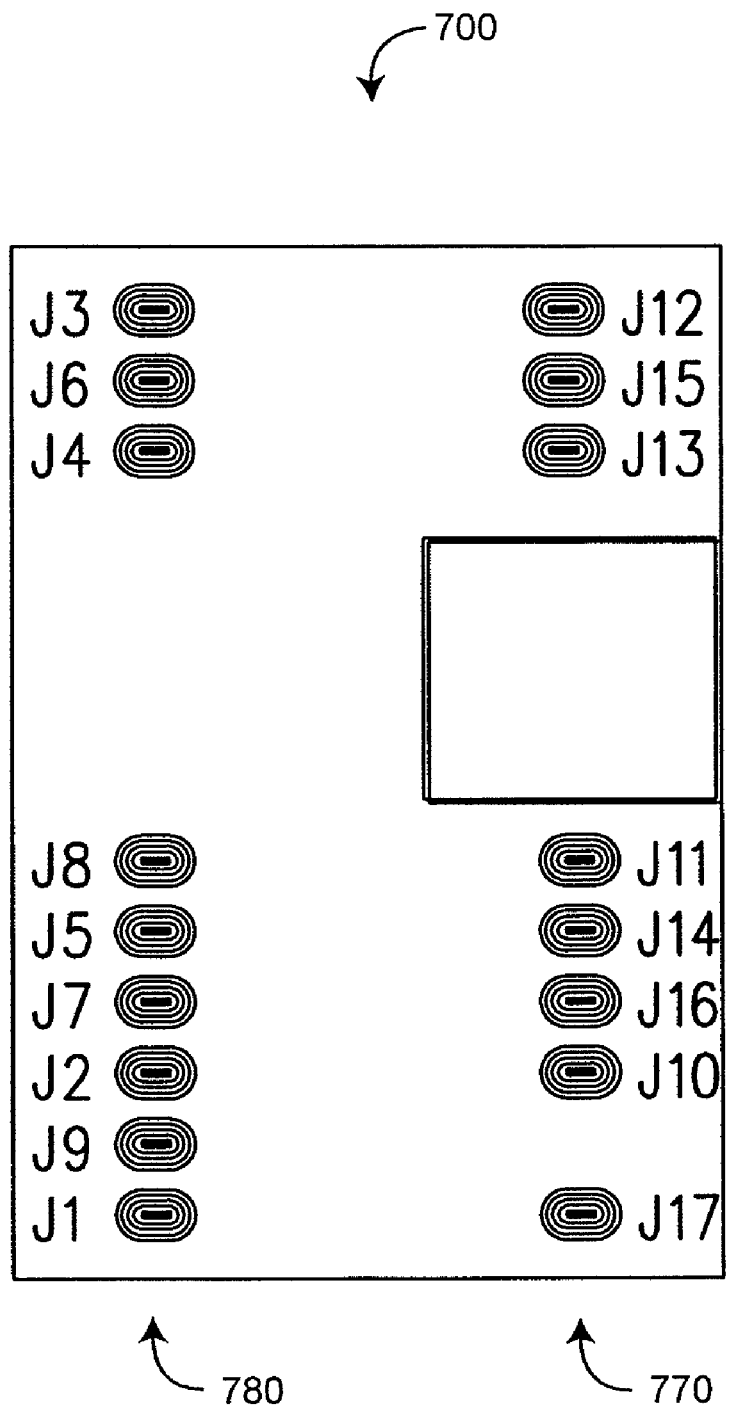
FIG. 7B is a top layout view of a duo connector circuit board.

FIGS. 7A-B illustrate an adapter circuit 600 and a corresponding circuit board 700. As shown in FIG. 7A, an adapter circuit 600 embodiment has array lines 612, a control 620 and a network 630, as described with respect to FIG. 6, above. The adapter circuit 600 also has switch 660 and an EEPROM 670, as described with respect to FIG. 6, above. The array lines 612, control 620 and network 630 connect to a monitor 50 (FIG. 6) via monitor-side pads 780. The array lines 612 and network 630 also connect to a sensor 10, 20 (FIG. 6) via sensor-side pads 770. Switches 660 include a first switch IC 662 and a second switch IC 664 each having dual single-pole, double-throw switches responsive to the control 620. In an embodiment, the switch ICs 662, 664 are each MAX 4684 available from Maxim Integrated Products, Inc., Sunnyvale, Calif. ("Maxim"). In an embodiment, the network 630 is a single wire, and the EEPROM is a DS2431X, also available from Maxim. As shown in FIG. 7B the circuit board 700 has a plurality of solder pads 770, 780 adapted for wire connections. Sensor-side pads 770 accommodate jumper wires 810 (FIG. 8A) to duo connector pins. Monitor-side pads 780 accommodate wires from the cable 350 (FIG. 3).

Also shown in FIG. 7A, when the control 620 is asserted, the four switches route a combination of cathode1 and anode1 signal and a combination of cathode2 and anode2 signal to the IR and red cathodes 614, respectively. In this manner, the monitor can activate the back-to-back LEDs as if connected in an array. That is, an IR LED is activated by pulling up cathode1 and current sinking anode2 and a red LED is activated by pulling up cathode 2 and current sinking anode1. When the control 620 is not asserted, the first switch IC 662 grounds the IR and red cathode lines 614. In this manner, when a SpO2 sensor is not connected, the drive lines proximate to the detector lines are grounded, so as to reduce the possibility of signal crosstalk inducing noise on the detector signal, as described above.

Figure 8C:
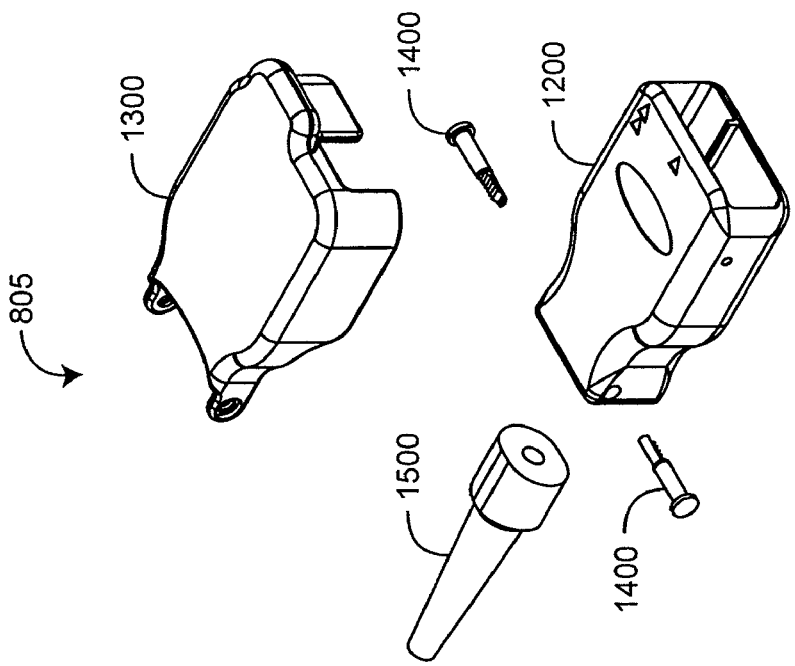
FIGS. 8A-C are perspective views of duo connector assemblies.
Figure 8B:
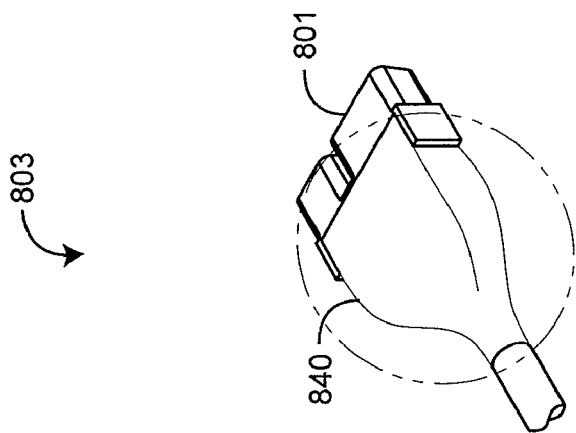
Figure 8A:
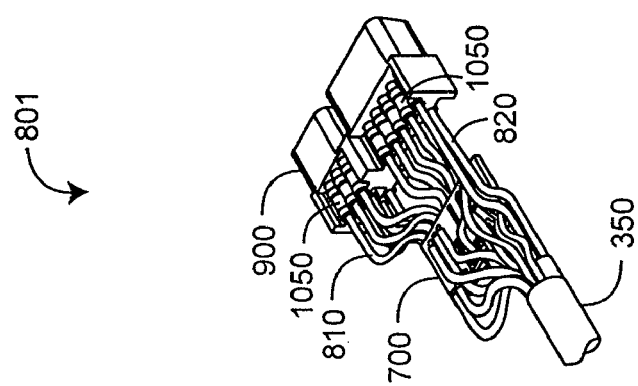
Figure 9B:
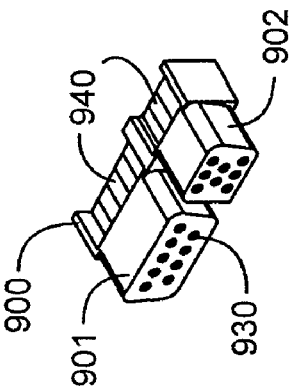
FIGS. 9A-D are top, perspective, front and side views, respectively, of a duo connector socket.
Figure 9D:
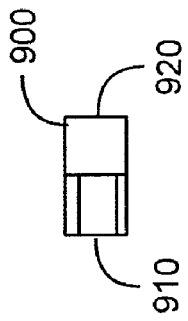
Figure 9A:
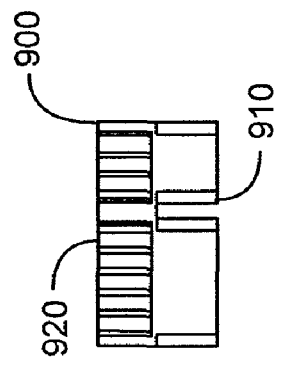
Figure 9C:
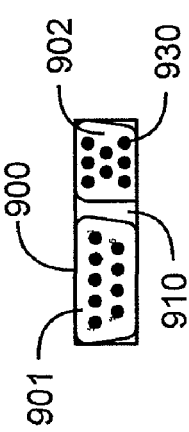
Figure 15B:
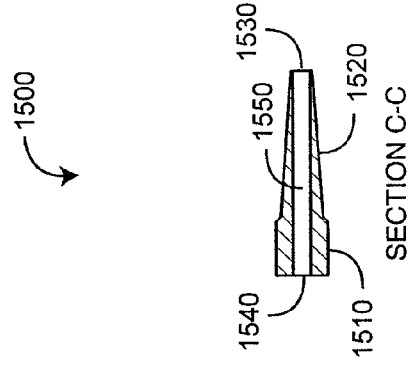
FIGS. 15A-D are top, side cross sectional, front and side views, respectively, of a duo connector strain relief.
Figure 15D:
Figure 15A:
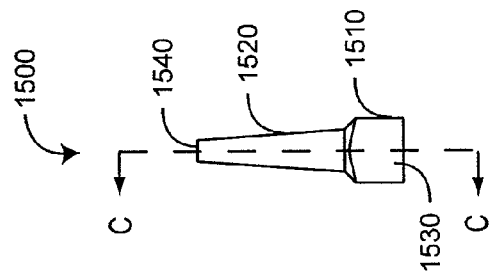
Figure 15C:
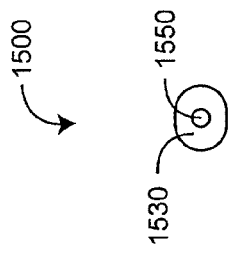

FIGS. 8A-C illustrate duo connector assemblies including a wiring assembly 801, a shielded wiring assembly 803 and a shell assembly 805. As shown in FIG. 8A, the wiring assembly 801 includes a circuit board 700, a socket 900, a cable 350, jumper wires 810, cable wires 820 and socket pins 1050. A first portion of the cable wires 820, including detector wires and a first portion of array drive wires, extend to the socket pins 1050. A second portion of the cable wires 820, including a network wire, a control wire, and a second portion of the array drive wires, extend to monitor-side pads 780 (FIG. 7B) of the circuit board 700. The jumper wires 810 extend between the sensor-side pads 770 (FIG. 7B) of the circuit board 700 and the socket pins 1050 and include the red and IR cathode drive wires and the network wire. The socket 900 is described in detail with respect to FIGS. 9A-D, below. The socket pins 1050 are described with respect to FIGS. 10-11, below.

As shown in FIG. 8B, the shielded wiring assembly 803 has a socket overmold 840 sealing the wiring assembly 801 so that no wires are exposed. The overmold is covered with a copper shield, which is grounded to the cable outer shield 526 (FIG. 5C). In an embodiment, the socket overmold 820 is a PVC material.

As shown in FIG. 8C, the shielded wiring assembly 803 is housed in the shell assembly 805. The shell assembly 805 has a shell 1200, a retainer 1300, hinge pins 1400 and a bend relief 1500. The shell 1200 encloses the shielded wiring assembly 803. The retainer 1300 is hinged to the shell 1200 so as to removably retain either of the sensor connectors 15, 1800 (FIG. 3). The hinge pins 1400 secure the retainer 1300 to the shell 1200. The bend relief 1500 protects the cable and cable wires proximate the shell 1200. In an embodiment, the shell 1200 and the bend relief 1500 are overmolded to the shielded wiring assembly 803. In a particular embodiment, the shell and bend relief overmolds are cast at the same time so that the bend relief 1500 is fused to the shell 1200. The shell 1200 is described in further detail with respect to FIGS. 12A-E, below. The retainer 1300 is described in further detail with respect to FIGS. 13A-E, below. The hinge pins 1400 are described in further detail with respect to FIGS. 14A-E. The bend relief 1500 is described in further detail with respect to FIGS. 15A-D, below.

FIGS. 9A-D illustrate a socket 900 having a front 910, a back 920, socket sections 901, 902 proximate the front 910, socket apertures 930 arranged in rows and extending through the socket sections 901, 902 and pin holders 940 proximate the back 920 also arranged in rows corresponding to the socket apertures 930. Each socket aperture 930 accepts a socket pin 1050 (FIG. 10D), which mates with corresponding plug pins extending from a sensor plug 15, 1800 (FIG. 3B). Wiring of the socket 900 and socket pins 1050 (FIG. 10D) are described above with respect to the wiring assembly 801 (FIG. 8B). Socket pins including shielded detector sockets 1000 (FIG. 10A) are described in detail with respect to FIGS. 10-11, below.

FIGS. 10A-D illustrate a socket pin 1050 and a shielded detector socket 1000 utilizing the socket pin 1050. The socket pin 1050 has a crimp 1052 for attaching wires and a body 1054 for receiving a mating connector pin. In an embodiment, the socket pin 1050 is a phosphor bronze with gold over nickel plating. A detector socket 1000 has a socket pin 1050, an insulating shroud 1100 and a shield 1150. The two detector lines 522 (FIG. 5C) are terminated at two corresponding detector sockets 1000, with the shield 1150 extending from the socket apertures 930 (FIGS. 9B-C) proximate the pin holders 940 (FIG. 9B) and connected to the cable inner shield 524 (FIG. 5C).

FIGS. 11A-C illustrate the detector socket shroud 1100 and shield 1150. The shroud 1100 accepts a socket pin body 1054 (FIG. 10D) and fits within the shield 1150. In an embodiment, the shroud 1100 is polypropylene or DuPont Delrin®, and the shield is copper.

FIGS. 12A-E illustrate a duo connector shell 1200 that houses a shielded wiring assembly 803 (FIG. 8B) including a socket 900. The shell 1200 is a generally rectangular enclosure having a front 1201, a back 1202, a top 1203 and a bottom 1205. The shell 1200 is tapered proximate the back 1202 which is narrower than the front 1201. On the top 1203, the shell 1200 has arrow indicators 1210 proximate the front 1201 and an artwork recess 1220. On both sides 1207, the shell 1200 has hinge apertures 1230 and depressions 1240. The front 1201 accommodates the socket sections 900 which accepts corresponding sensor connectors 15, 1800 (FIG. 3B). The back 1202 accommodates a patient cable 350 (FIG. 3B) which is supported to proximate the shell 1200 by a bend relief 1500 (FIGS. 15A-D). The arrow indicators 1210 match with corresponding sensor connector indicators 16, 1803 (FIG. 3B) providing a sensor connector alignment guide, as described with respect to FIG. 3B, above. The hinge apertures 1230 accommodate the hinge pins 1400 (FIGS. 14A-E) that attach the retainer 1300 (FIGS. 13A-E) to the shell 1200, as described with respect to FIGS. 4A-F, above. The depressions 1240 accept corresponding retainer protrusions 1340 (FIG. 13B) so as to releasably hold the retainer 1300 in a closed position shown in FIGS. 4A-D. In an embodiment, the shell 1200 is overmolded on the shielded wiring assembly 803 (FIG. 8B), including the socket 900. In an embodiment, the shell 1200 is medical grade PVC of 90-100 Shore A durometer.

FIGS. 13A-E illustrate a duo connector retainer 1300 configured to hinge to the shell 1200 (FIGS. 12A-E) so as to removably retain sensor connectors 15, 1800 (FIG. 3B). The retainer 1300 is a generally rectangular cover having a front 1301, a back 1302, a top 1303 and a bottom 1305 and is configured to fit at least partially over the shell front 1201, top 1203 and sides 1207 (FIGS. 12A-E). Proximate the front and top 1301,1303, the retainer 1300 has a protruding tab 1310 that accommodates a person's finger or thumb to easily open or close the retainer. Protruding from the retainer back 1302 and proximate the retainer sides 1307 are hinges 1320, each having a hinge aperture 1330 configured to match up with corresponding shell hinge apertures 1230 (FIG. 12E) so as to accommodate hinge pins 1400 (FIGS. 14A-E). Extending inwardly from the retainer sides 1307 are protrusions 1340 (FIG. 13B) configured to click into corresponding shell depressions 1240 (FIG. 12E) so as to releasably hold the retainer 1300 in a closed position (FIGS. 4A-D). The front 1301 has a cable aperture 1350 offset from the tab 1310 and configured to accommodate sensor cables immediately behind the sensor connectors 15, 1800 (FIG. 3B) to prevent inadvertent disconnection of sensors 10, 20 (FIGS. 3A-B) from the duo connector 400 (FIG. 3B). In an embodiment, the retainer 1300 is a medical grade clear plastic.

FIGS. 14A-E illustrate a duo connector hinge pin 1400 that rotatably attaches the retainer 1300 (FIGS. 13A-E) to the shell 1200 (FIGS. 12A-E). In particular, a pair of pins 1400 insert through retainer apertures 1220 (FIGS. 12A-E) and shell apertures 1320 (FIGS. 13A-E) from opposite directions and are fixedly latched together. The pin 1400 has a generally round head 1410, a cylindrical shaft 1420 extending generally normal to the head 1410, and a partially cylindrical latching portion 1430 extending from the end of the shaft 1420 distal the head 1410. A plurality of teeth 1432 are disposed on the latching portion 1430. The teeth 1432 are configured to slide past corresponding teeth on an opposite pin 1400 in one direction only, so as to latch together opposite facing pins. So disposed, the pin heads 1410 hold the shell 1200 (FIGS. 12A-E) relative to the retainer 1300 (FIGS. 13A-E) as the retainer rotates about the pin shafts 1420.

FIGS. 15A-D illustrate a bend relief 1500 that protects the cable from bending forces and the cable wires and corresponding solder joints from pulling forces. The bend relief 1500 is a generally tapered cylinder having a head 1510, a tail 1520, a front 1530, a back 1540 and an axial cavity 1550 extending the length of the bend relief. In an embodiment, the bend relief 1500 is overmolded on the patient cable 350 (FIG. 3B) so that the cable 350 is retained within the axial cavity 1550 so formed. The head 1510 is disposed proximate the shell back 1202 (FIGS. 12A-E), with the tail 1520 extending distal the shell 1200 (FIGS. 12A-E). In an embodiment, the bend relief 1500 is medical grade PVC having a 40-50 Shore A durometer. In an embodiment, the bend relief 1500 and shell 1200 are overmolded at the same time so that the bend relief front 1530 fuses to the shell back 1202 (FIGS. 12A-E).

A duo connector patient cable has been disclosed in detail in connection with various embodiments. These embodiments are disclosed by way of examples only and are not to limit the scope of the claims that follow. One of ordinary skill in art will appreciate many variations and modifications.

What is claimed is:

1. In a patient monitoring system having a sensor configured to transmit at least two wavelengths of optical radiation into a tissue site and detect the radiation after attenuation by pulsatile blood flowing within the tissue site, a patient monitor configured to process a signal responsive to the detected radiation and generate at least one parameter indicative of a patient physical condition, a patient cable for interconnecting the sensor and patient monitor comprising:

a monitor connector configured to mate with a corresponding connector in a patient monitor;

a sensor connector configured to mate with either of two different types of corresponding sensor connectors, the sensor connector including a first socket section configured to mate with only a first corresponding sensor connector type and a second socket section configured to mate with only a second corresponding sensor connector type, the first and second socket sections housed in the same housing, wherein the first socket section is configured to mate with a first sensor and the second socket section is configured, along with the first socket section, to mate with a second sensor; and a cable interconnecting the monitor connector and the sensor connector so as to transmit drive signals originating from the monitor to the sensor and to transmit sensor signals originating from the sensor to the monitor.

2. The patient cable according to claim 1 wherein:
   the first sensor is a two-wavelength pulse oximeter sensor; and
   the second sensor is a multiple wavelength sensor capable of transmitting more than two wavelengths of optical radiation into a tissue site.

3. The patient cable according to claim 2 further comprising a circuit for converting multiple wavelength sensor drive signals into two-wavelength sensor drive signals.

4. The patient cable according to claim 3 wherein the circuit comprises:
   a circuit board housed in the sensor connector; and
   a plurality of switches mounted to the circuit board,
   wherein the switches route portions of array drive signals generated by the monitor to back-to-back drive signal pins in communications with the two-wavelength sensor.

5. The patient cable according to claim 4:
   wherein the back-to-back signal drive pins are housed in the first socket section, and
   wherein the array drive signals for the multiple wavelength sensor are communicated to the second section.

6. The patient cable according to claim 5 further comprising:
   detector signal pins housed in the first socket section in communications with either the two-wavelength sensor or the multiple wavelength sensor when attached,
   wherein drive signal pins housed in the first section are grounded when the multiple wavelength sensor is attached so as to improve noise isolation of the detector signal.

7. A patient cable method comprising the steps of:
   providing a duo sensor connector having a first socket section and a second socket section housed in the same housing and proximate to each other;
   removably attaching a first sensor having a conventional connector to the first socket section for making pulse oximetry measurements; and
   removably attaching a second sensor having a mating duo connector to the first and second socket sections for making blood parameter measurements in addition to pulse oximetry measurements, wherein the first and the second sensors are not attached at the same time.

8. The patient cable method according to claim 7 comprising the further steps of:
   communicating first drive signals to the first socket section; and
   communicating second drive signals to the second socket section,
   wherein a portion of the second drive signals are routed to the first socket section as the first drive signals when the first sensor is attached to the duo sensor connector.

9. The patient cable method according to claim 8 comprising the further step of converting second drive signals from a multiple parameter patient monitor configured for an LED array to first drive signals configured for back-to-back LEDs when the first sensor is attached to the duo sensor connector.

10. The patient cable method according to claim 9 comprising the further step of switching signals between pins in the first socket section and the second socket section within the duo sensor connector.

11. The patient cable method according to claim 10 comprising the further step of grounding drive signal pins in the first socket section when the second sensor is attached to the duo sensor connector so as to provide noise isolation of detector signal pins in the first socket section.

* * * * *

UNITED STATES PATENT AND TRADEMARK OFFICE
CERTIFICATE OF CORRECTION

PATENT NO. : 8,315,683 B2  
APPLICATION NO. : 11/858818  
DATED : November 20, 2012  
INVENTOR(S) : Ammar Al-Ali Page 1 of 1

It is certified that error appears in the above-identified patent and that said Letters Patent is hereby corrected as shown below:

In the Specification

In Column 3, Lines 33-34, change "a WTM" to --a--.

In Column 6, Line 37, change "15,1800" to --15, 1800--.

In Column 7, Line 48, change "1301,1303," to --1301, 1303,--.

Signed and Sealed this  
First Day of July, 2014

Michelle K. Lee  
*Deputy Director of the United States Patent and Trademark Office*